US008403975B2

(12) United States Patent
Hadas (10) Patent No.: US 8,403,975 B2
(45) Date of Patent: Mar. 26, 2013

(54) ARRANGEMENT FOR AND METHOD OF COLD THERAPY TREATMENT

(75) Inventor: Susan Laurel Hadas, Oceanside, NY (US)

(73) Assignee: Personally Cool Inc., Oceanside, NY (US)

( * ) Notice: Subject to any disclaimer, the term of this patent is extended or adjusted under 35 U.S.C. 154(b) by 309 days.

(21) Appl. No.: 12/700,149

(22) Filed: Feb. 4, 2010

(65) Prior Publication Data

US 2010/0217364 A1    Aug. 26, 2010

Related U.S. Application Data

(60) Provisional application No. 61/208,426, filed on Feb. 24, 2009.

(51) Int. Cl.
*A61F 7/02* (2006.01)
(52) U.S. Cl. ............ 607/114; 607/96; 607/108; 607/112
(58) Field of Classification Search .................... 607/96, 607/108, 112, 114
See application file for complete search history.

(56) References Cited

U.S. PATENT DOCUMENTS

| | | | |
|---|---|---|---|
| 3,871,376 A * | 3/1975 | Kozak ........................ 604/291 |
| 4,266,407 A | 5/1981 | Gibson | |
| 4,592,358 A * | 6/1986 | Westplate ..................... 607/112 |
| 5,237,838 A * | 8/1993 | Merritt-Munson .......... 62/457.2 |
| 5,314,005 A * | 5/1994 | Dobry ............................. 165/10 |
| 5,701,757 A | 12/1997 | Heverly | |
| 5,840,080 A * | 11/1998 | Der Ovanesian ............ 607/114 |
| 7,228,712 B1 | 6/2007 | Stegenga | |
| 2005/0262871 A1 | 12/2005 | Bailey-Weston | |
| 2006/0032266 A1 | 2/2006 | Gagnon | |
| 2008/0066491 A1 | 3/2008 | Russo | |
| 2008/0141700 A1 | 6/2008 | Fuchs | |

FOREIGN PATENT DOCUMENTS

| | | |
|---|---|---|
| EP | 0123949 | 11/1984 |
| EP | 0162583 | 11/1985 |

* cited by examiner

*Primary Examiner* — Linda Dvorak
*Assistant Examiner* — Jared W Pike
(74) *Attorney, Agent, or Firm* — Kirschstein, et al.

(57) ABSTRACT

An arrangement for, and a method of, cooling a body site, especially for treating menopause-associated vasomotor symptoms, places one or more cold packs in a thermally insulated housing in which a cold source is present, and cools each cold pack by placement of the housing, either opened or closed, in a freezer or like apparatus. The cold packs retain their cold temperature prior to onset of a condition requiring cold therapy relief by the presence of the cold source and the thermally insulating properties of the housing. Each cold pack is removable from the housing after onset of the condition, is externally applied to a user experiencing the condition requiring cold therapy relief, and is re-usable.

21 Claims, 4 Drawing Sheets

ARRANGEMENT FOR AND METHOD OF COLD THERAPY TREATMENT

CROSS REFERENCE TO RELATED APPLICATION

This application claims the benefit of U.S. Provisional Patent Application Ser. No. 61/208,426, filed Feb. 24, 2009, which is hereby incorporated by reference herein.

DESCRIPTION OF THE RELATED ART

This invention relates generally to a kit or arrangement for, as well as a method of, treating a person with cold therapy, especially beneficial when treating hot flashes associated with menopausal women.

It is estimated that as many as three out of every four women experience hot flashes as they go through the menopausal transition, which is typically characterized by one or more of such menopause-associated vasomotor symptoms as a feeling of mild warmth to intense heat spreading through a woman's upper body and face, a flushed appearance with red, blotchy skin on the woman's face, neck and upper chest, a rapid heartbeat, and perspiration, mostly on the woman's upper body. Hot flashes vary in frequency and intensity, for example, from full-on sweating throughout the day and night (night sweats), or just occasionally feeling warmer than normal. Hot flashes can last as long as thirty minutes, but most subside within a couple of minutes. Hot flashes are common during perimenopause—the period of time leading up to menopause—and tend to peak during the first couple of years after menstrual periods have stopped. For some women, hot flashes last up to a couple of years. For others, hot flashes may continue for several years, or indefinitely.

Typically, hot flashes can have substantial or even debilitating adverse effects on affected women, and have been treated with hormones, exercise, diet, stress-reducing techniques, paced respiration, and cold therapy to reduce the body's core temperature. However, hormone treatment may be associated with numerous serious side effects. Exercise and diet regimens or controlled breathing may not be altogether available or effective against a sudden hot flash. Cold therapy by the application of cold packs to the body has been found to be beneficial against a sudden hot flash requiring instant relief.

To that end, U.S. Pat. No. 5,956,963 discloses a wrist cooler that offers relief for hot flash symptoms of menopause and body overheating. The cooler includes chemical cooling pellets that remain in a solid state until broken. When a hot flash occurs, the pellets are broken, and the cooler is slid onto a wearer's wrist. Once the flash has subsided, the cooler is removed from the wrist and is discarded and not re-used. Since the wearer's wrist is often in plain sight of others, wearing such wrist coolers may indicate to others, to the detriment and embarrassment of the wearer, that the wearer is experiencing a hot flash.

U.S. Patent Publication No. 2003/0176904 discloses a self-adhering cotton fabric cold strip having a cooling gelatinous material that is to be worn as a wristband, or an ankle band. An adhesive adheres the cold strip to the skin surface of a wearer. The cold strip is worn for a few hours and is then peeled off of the wearer's skin, discarded and not re-used. Wearing such a cold strip can be embarrassing and uncomfortable to the wearer, and peeling off the adhered cold strip can be irritating to the wearer's skin.

U.S. Patent Publication No. 2007/0098769 discloses a kit for treating hot flashes and includes a self-adhering patch for application to a wearer's skin, for example, behind the wearer's back between her shoulder blades. Due to the difficulty of reaching this location, the woman often needs help in securing the patch into position, and wears the patch underneath her clothes for extended time periods, even before onset of the hot flashes. Certain clothing may not adequately conceal the patch, thereby leading to embarrassment, and the prolonged wearing of the patch can lead to discomfort.

As advantageous as the known cold therapy treatments have been in controlling and/or reducing hot flash symptoms in menopausal women, they have not proven to be altogether satisfactory in use. One cannot re-use a cold pack with broken chemical pellets, or readily re-attach an adhesive patch, especially over irritated skin. The cold packs that are worn, typically with discomfort, in plain sight of others are embarrassing to wear, especially in a business setting. A cold pack that is worn for extended time periods, or even a refrigerated cold pack that is held in a woman's purse for subsequent use when needed, cools down and eventually becomes ineffective as a cooler, especially for a hot flash that occurs hours later.

SUMMARY OF THE INVENTION

One feature of the present invention resides, briefly stated, in an arrangement for treating a person with cold therapy at a human body site requiring to be cooled. The body site can be, for example, an injured or swollen area, an area made hot after exposure to radiation or chemotherapy, an area made hot after physical exertion as in exercise, work, or manual labor, or, in a preferred application, any woman's body site experiencing menopause-associated vasomotor symptoms. The arrangement includes one or more cold packs for external application, either directly or indirectly, to the body site of a woman experiencing a hot flash, and a thermally insulated housing in which each cold pack is held and maintained at a cold temperature, e.g., ranging from a sub-freezing temperature of about 17 degrees Fahrenheit to about 55 degrees Fahrenheit. Each cold pack is preferably re-usable and comprises a bag made of a flexible, sheet plastic material that contains an aqueous gel having water-swellable polymeric components that are cooled to the cold temperature to cool the body site of the woman during external application of each cold pack, and a disposable sanitary cover or sleeve in which the bag is contained during external application to the body site of the woman. Each cold pack remains malleable at sub-freezing temperatures, that is, is not frozen solid at the cold temperature for the woman's comfort during conforming application against the body site. The cover serves not only as a soft, cold- and moisture-moderating barrier, but also to absorb sweat, oils, cosmetics and the like.

Advantageously, a cold source is also held, either removably or permanently, in the thermally insulated housing in a cooling relationship with each cold pack to help maintain each cold pack at the cold temperature. The preferred cold source also contains an aqueous gel having water-swellable polymeric components. The cold source preferably has a greater mass than each cold pack, and preferably is formulated to be frozen solid at the cold temperature. The cold source is not intended for application to the body site. Thus, the cold source, as well as the thermally insulating properties of the housing, keeps each cold pack at the cold temperature for a longer time in the thermally insulated housing than if the cold source and/or the thermally insulated housing were not present or used alone. The cold source may be configured as a pouch or bag made of a flexible, sheet plastic material, or, in another preferred embodiment, the cold source may be configured as a hollow, blow-molded plastic component in which the gel is contained. Other cold sources, including electronic cold-generating sources, are also contemplated.

The thermally insulated housing may have a clamshell design with one compartment for receiving at least one of the cold packs, and another compartment for receiving the cold source. In this embodiment, the compartments lie side-by-side and the cold packs are spaced apart from the cold source in an opened condition of the housing, and the compartments overlie each other and the cold packs contact the cold source in a closed condition of the housing. Alternatively, in another embodiment, the cold source may be mounted in a central region of the thermally insulated housing, and one of the cold packs could be mounted at one side, e.g., above, the cold source, and the other of the cold packs (if two cold packs are used) could be mounted at the opposite side, e.g., below, the cold source, in a closed condition of the housing.

A user preferably places the housing, either opened or closed, in a freezer or like apparatus for a cooling time period sufficient to cool the cold packs and to simultaneously cool the cold source. Preferably, the user places the sleeves on each cold pack prior to said cooling. When readying the arrangement for use, the user places the closed housing with the sleeved cold packs and cold source inside in her purse, pocket, briefcase, backpack, vehicle glove box, or analogous transport device for transport with her. Upon onset of a hot flash or other condition requiring cold therapy relief, the housing is removed from the transport device, and each sleeved cold pack, which is still cold due to the cold source, as well as the thermally insulating properties of the housing, is removed from the housing and externally applied to the user's skin site where cooling relief is desired.

Another aspect of the invention resides in a method of treating a person with cold therapy at a human body site requiring to be cooled, especially for treating menopause-associated vasomotor symptoms. The method is performed by placing each cold pack in a housing that may or may not be thermally insulated, cooling each cold pack and a cold source in the same housing to a cold temperature in the housing, retaining each cold pack in the housing to maintain the cold temperature, removing each cold pack from the housing after onset of the condition requiring cold therapy relief, and externally applying the removed cold pack to the user's body site. Each cold pack, as well as the cold source, is re-usable and preferably each cold pack is encased in a sleeve prior to the external application. The cooling step is performed in an opened or a closed condition of the housing by placement of the housing in a freezer or like apparatus for a cooling time period.

Thus, this invention does not break any chemical pellets, or use any adhesive patches, or cause any undue embarrassment or discomfort, as taught by the prior art. Each cold pack of this invention is not worn, and can be held and easily transported for extended time periods for subsequent use when needed, without each cold pack warming up and being ineffective.

The novel features which are considered as characteristic of the invention are set forth in particular in the appended claims. The invention itself, however, both as to its construction and its method of operation, together with additional objects and advantages thereof, will be best understood from the following description of specific embodiments when read in connection with the accompanying drawings.

DETAILED DESCRIPTION OF THE PREFERRED EMBODIMENTS

Figure 1:
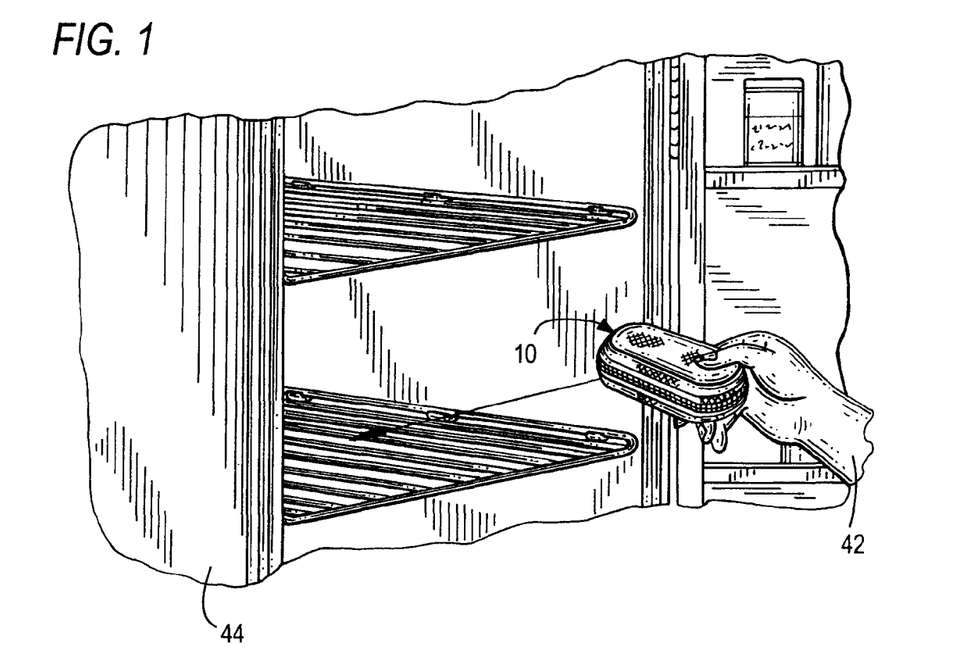
FIG. 1 is a perspective view of one embodiment of an arrangement for providing cold therapy relief, e.g., by treating menopause-associated vasomotor symptoms, the arrangement being placed in a freezer or like apparatus in accordance with a method of this invention.
Figure 2:
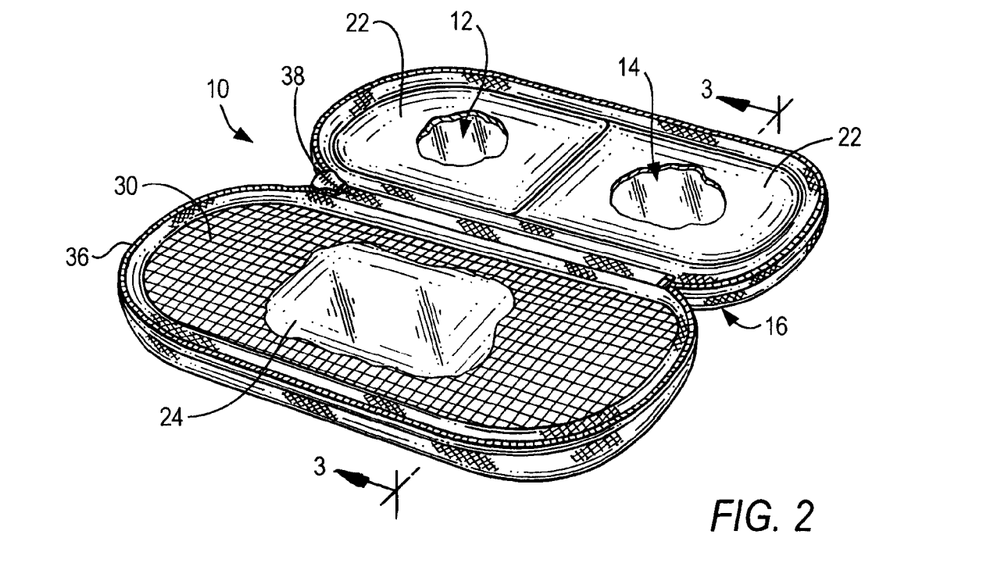
FIG. 2 is an enlarged, partly broken away, perspective view of the embodiment of FIG. 1 in an opened condition.
Figure 3:
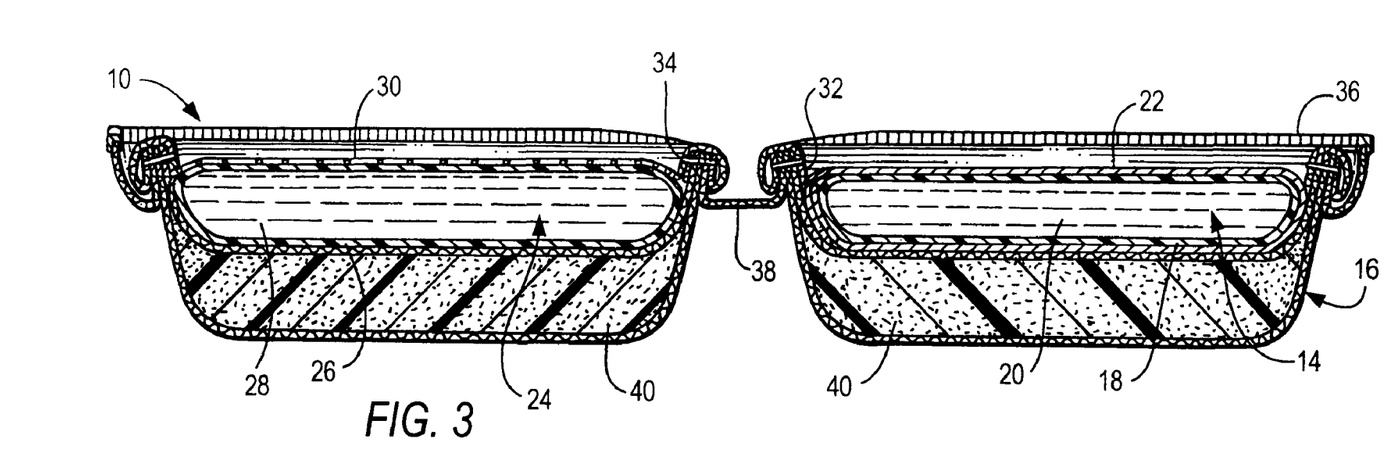
FIG. 3 is an enlarged, sectional view taken in the direction of the arrows on the line 3-3 of FIG. 2.

Referring now to FIGS. 1-3 of the drawings, reference numeral 10 generally identifies one embodiment of an arrangement for cooling a human body site, especially for treating menopause-associated vasomotor symptoms. Arrangement 10 includes a pair of cold packs 12, 14, each available for external application, either directly or indirectly, to the body site needing cold therapy relief, e.g., a body site of a woman experiencing a hot flash, and a thermally insulated housing 16 in which the cold packs 12, 14 are held prior to onset of the hot flash.

Each cold pack 12, 14 is preferably re-usable and comprises a bag 18 (see FIG. 3) made of a flexible, sheet plastic, film-like material and containing an aqueous gel 20 having water-swellable polymeric components, as described in detail below, that are cooled to a cold temperature to cool the body site during external application of each cold pack 12, 14, and a disposable sanitary sleeve or cover 22 in which the respective bag 18 is inserted and contained during external application to the woman. Each cold pack 12, 14 remains malleable, that is, not frozen solid, at the cold temperature for the woman's comfort during conforming application against the body site.

The cover 22 is preferably a casing of sheet material and constituted of a soft paper, cotton, or other fibrous material, preferably provided with a moisture barrier film, for comfort to prevent the bag 18 from direct, uncomfortably cold and/or slick, contact with the woman's site. The cover 22 is advantageously biodegradeable and is intended for single use only. The cover 22 serves not only as a soft, cold- and moisture-moderating barrier, but also to absorb sweat, oils, cosmetics and the like. The cover 22 may also have straps, a finger hole, a slit or analogous holder to allow the woman to insert one or more fingers thereunder to more securely hold the covered cold pack in place during its application. Broken-away portions of the cover 22 in FIG. 2 reveal the cold packs 12, 14 thereunder.

Arrangement 10 also preferably includes a cold source configured as a pouch 24 (see FIG. 2), also held in the thermally insulated housing 16. The cold pouch 24 is re-usable and comprises a bag 26 made of a flexible, sheet plastic, film-like material and containing an aqueous gel 28 having water-swellable polymeric components, as described in detail below. The cold pouch 24 preferably has a greater mass than each cold pack 12, 14, and preferably is formulated to be frozen solid at the cold temperature. The cold pouch is not intended for application to the body site. A restrainer, such as the illustrated mesh 30, preferably of a stretchable or non-stretchable material, overlies and retains the cold pouch 24 in the housing 16. The cold pouch 24 is preferably removable from the restrainer, for example, through a side opening in the mesh 30. Broken-away portions of the mesh 30 in FIG. 2 reveal the cold pouch 24 thereunder.

The thermally insulated housing 16 has a hinged clamshell design with one compartment 32 for receiving at least one, and preferably both, of the cold packs 12, 14, and another compartment 34 for receiving the cold pouch 24. The compartments 32, 34 lie side-by-side and the cold packs 12, 14 are spaced side-by-side apart from the cold pouch 24 in an opened condition of the housing 16 shown in FIG. 3, and the compartments 32, 34 overlie each other and the cold packs 12, 14 contact the cold pouch 24 in a closed condition of the housing 16 shown in FIG. 1. The housing 16 preferably has a fastener, such as a thermally insulated, covered zipper 36, bounding the compartments 32, 34 and a hinge 38 about which the compartments 32, 34 are foldable between the closed and opened conditions. Thermal insulation, such as foam 40, overlie the compartments 32, 34 at the exterior of the housing 16 and resist heat from the exterior of the housing entering therein and warming the cold packs 12, 14.

As shown in FIG. 1, a user 42 preferably places the housing 16 with the cold packs 12, 14 and with the cold pouch 24 inside the housing 16 in a freezer or like apparatus 44 for a cooling time period sufficient to cool the cold packs 12, 14 and to simultaneously cool the cold pouch 24. Preferably, each cold pack 12, 14 is inserted into a respective sleeve 22 prior to the cooling. As shown in FIG. 1, the housing 16 is closed. This is a convenience for the user who does not want to be bothered with opening the housing 16 prior to placement in the apparatus 44 since it will take longer for the cold packs 12, 14 and the cold pouch 24 to cool when the housing 16 is closed. Yet, given enough time, for example, overnight, this can be accomplished. Less time is required for the cold packs 12, 14 and the cold pouch 24 to cool when the housing 16 is opened prior to placement in the apparatus 44.

To use the arrangement, the user 42 removes the housing 16 containing the sleeved cold packs 12, 14 and the cold pouch 24 from the apparatus 44 and, if necessary, closes the housing 16, and places the closed housing 16 in her purse, pocket, briefcase, backpack, vehicle glove box, or analogous transport device for transport with her. The cold pouch 24, as well as the thermal insulation 40 of the housing 16, keeps each cold pack 12, 14 at the cold temperature for a much longer time, for example, twelve hours, than if the thermal insulation 40 and/or the cold pouch 24 were not present or used alone. Upon onset of a condition requiring cold therapy relief, e.g., a hot flash, the housing 16 is removed, for example, from the transport device, and each sleeved cold pack 12, 14, which is still cold due to the cold pouch 24, as well as due to the thermal insulation 40, is removed from the housing 16 and externally applied to the user's skin where cooling relief is desired by removing heat from the user's skin.

Figure 4:
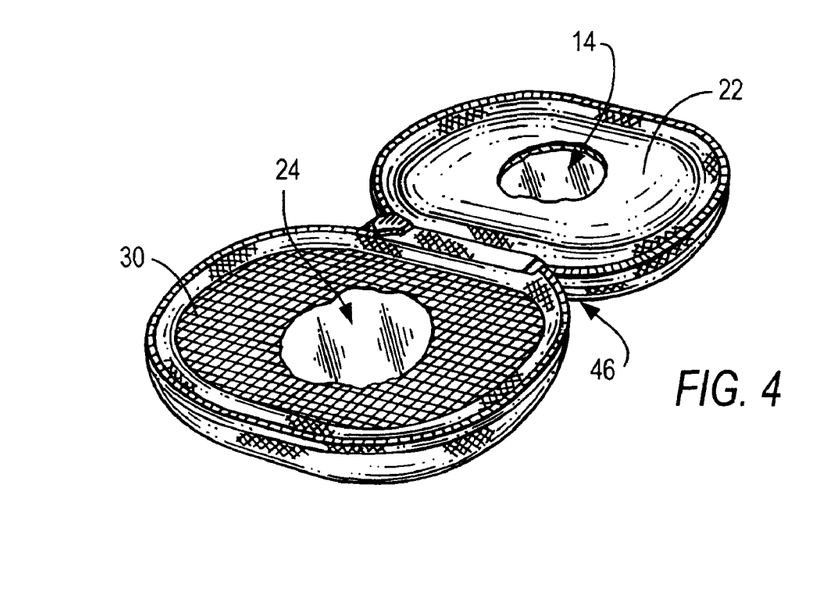
FIG. 4 is an enlarged, partly broken away, perspective view of another embodiment of an arrangement in accordance with this invention in an opened condition.

FIG. 4 depicts another, more compact embodiment of an arrangement 46 according to this invention, in which only a single cold pack 14 is mounted in one compartment of the housing, and a cold pouch 24 is mounted in the other compartment. The cold pack 14 may be of a smaller dimension, and the cold pouch 24 is of a smaller dimension, than in the arrangement 10.

Figure 5:
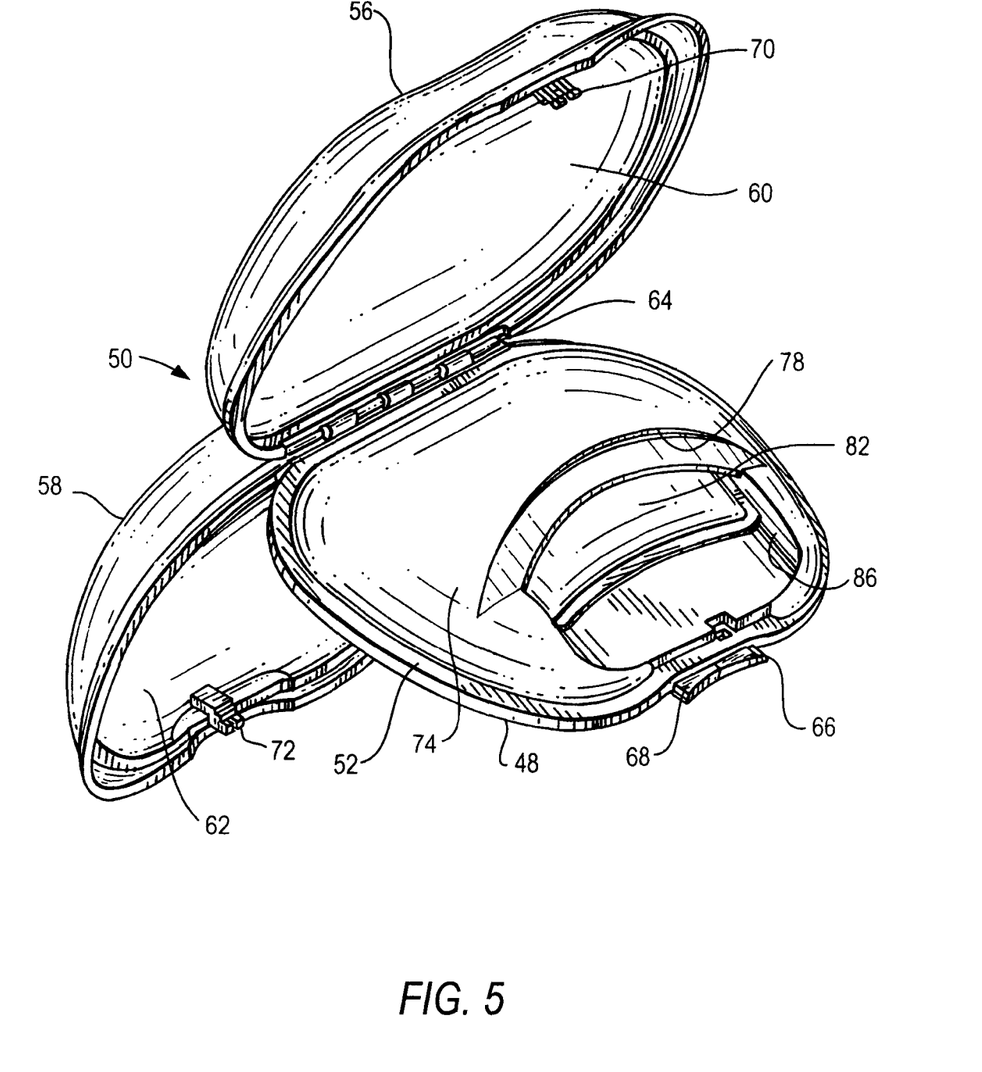
FIG. 5 is an enlarged, perspective view of still another embodiment of an arrangement in accordance with this invention in an opened condition.
Figure 6:
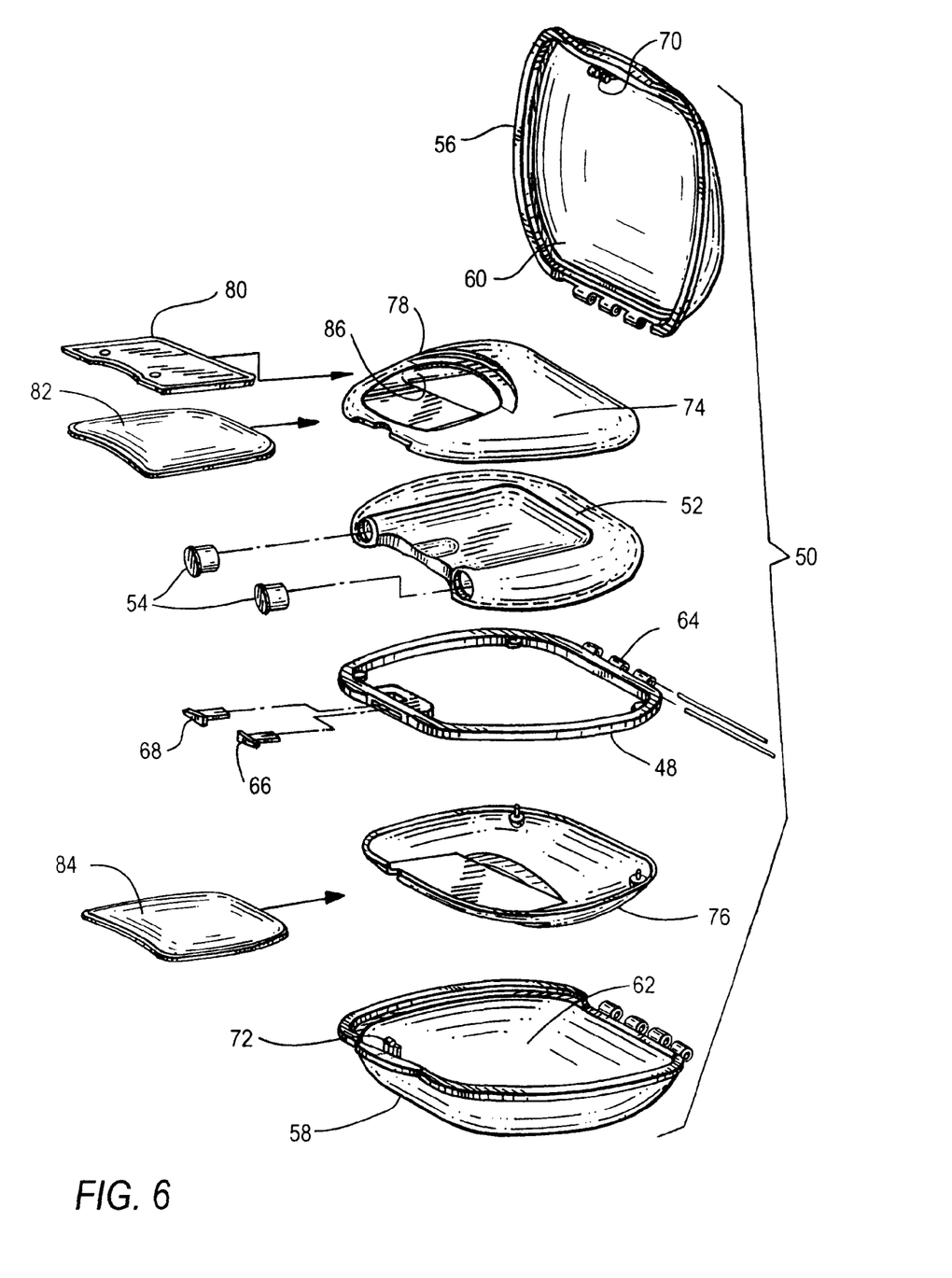
FIG. 6 is an exploded, perspective view of the embodiment of FIG. 5.

FIGS. 5-6 depict another, currently preferred, embodiment of an arrangement 50 according to this invention, in which the aforementioned cold source is configured as a hollow, blow-molded plastic component 52 in which the gel 28 (see FIG. 3) is contained and sealed therein by a pair of plugs 54. The cold component 52 is supported by an annular gasketed support 48 that is mounted in a core or central region of a thermally insulated housing having an upper shell 56 that is interiorly lined with a layer of insulation 60, and a lower shell 58 that is interiorly lined with a layer of insulation 62. The cold component 52 is sandwiched between upper and lower core covers 74, 76 and form a subassembly. As described below, this subassembly may be permanently mounted to the shells 56, 58, or may be removably mounted from the shells 56, 58. The shells 56, 58 and the support 48 are hinged together by a rear hinge 64 to enable either of the shells to be swung open, or even both shells, as shown in FIG. 5, to be swung open. A pair of latch releases 66, 68 cooperate with a pair of latches 70, 72 at front edges of the shells to release the shells for movement to the opened position.

A pair of cold packs 82, 84, analogous in structure and function to the aforementioned cold packs 12, 14, is inserted into, and removable from, openings 86 in each core cover. Thus, one of the cold packs, e.g., pack 82, is mounted at one side, e.g., above, the cold component 52, and the other of the cold packs, e.g., pack 84, is mounted at the opposite side, e.g., below, the cold component 52, in a closed condition of the housing. A packet of disposable sleeves, only one of which is shown in FIG. 6 and identified by the reference numeral 80, each sleeve being analogous in structure and function to the aforementioned sleeve 22, is inserted into, and removable from, respective openings 78 in each core cover.

The method of providing cold therapy relief, e.g., treating menopause-associated vasomotor symptoms according to one aspect of this invention, is performed by placing each cold pack 12, 14, 82, 84 in the respective thermally insulated housing, cooling each cold pack 12, 14, 82, 84 and the cold source 24, 52 in the housing to a cold temperature, retaining each cold pack 12, 14, 82, 84 in the thermally insulated housing prior to onset of a condition requiring cold therapy relief, e.g., a hot flash, removing each cold pack 12, 14, 82, 84 from the thermally insulated housing after onset of the condition, and externally applying the removed cold pack 12, 14, 82, 84 to a body site requiring cold therapy relief, e.g., a body site of a woman experiencing the hot flash, for example, on her wrist, behind the ear, or on her forehead. Each cold pack 12, 14, 82, 84 is re-usable. The removed cold pack is advantageously mounted in a disposable sleeve 22 prior to its external application. The cooling step is performed in an opened or a closed condition of the housing by placement of the housing in the freezer or like apparatus 44 for a cooling time period.

In a variant construction, rather than placing the entire thermally insulated housing in the freezer or like apparatus 44, only the aforementioned removable subassembly comprised of the cold component 52, the annular support 48 and the upper and lower core covers 74, 76, together with the cold packs 82, 84 and, preferably, with the packets of sleeves 80, is placed in the freezer or like apparatus 44 for the cooling time period. The core covers 74, 76 help to resist heat transfer away from the cold packs 82. 84. Thus, the subassembly itself can be considered the housing that is placed in the apparatus 44. The cooled subassembly can be returned to the shells 56, 58 after the cooling period. This variant is particularly beneficial when the shells 56, 58 are covered in a material, such as a fabric or leather.

Each aforementioned gel 20, 28 may comprise one or more water-swellable polymeric components swelled with water. Such water-swellable polymeric components are well known and are often referred to as hydrophilic polymeric components or materials, or hydrogel-forming polymeric components or materials. One very useful water-swellable polymeric component includes one or more polyacrylic acid components and the like. However, it should be noted that other formulations, and one or more other suitable water-swellable polymeric components may be used or included in the gels 20, 28, and such other formulations and other water-swellable polymeric component or components are included within the scope of the present invention. Each aforementioned gel 20, 28 may have a water content sufficient to swell the gel, for example, in a range of about 40% or about 60% or about 75% to about 95% by weight of the gel. Each gel 20, 28 advantageously is cooled to a cold temperature ranging from a sub-freezing temperature of about 17 degrees Fahrenheit to about 55 degrees Fahrenheit. The gel 20 advantageously is malleable at the cold temperature, while the gel 28 is formulated to be less malleable, if not frozen solid, at the cold temperature.

It will be understood that each of the elements described above, or two or more together, also may find a useful application in other types of constructions differing from the types described above. In its broadest aspect, a single cold pack is mounted in the insulated housing, and a cold source is not mounted in the housing. Alternately, two or more cold packs, for example, in side-by-side or in overlapping relation, can be mounted in the insulated housing, and a cold source is again not mounted in the housing. If a cold source is mounted in the housing, then the housing may contain one or more cold packs, and the cold source may be mounted, for example, in side-by-side or in overlapping relation, with one or more of the cold packs, or preferably the cold source may be sandwiched between two cold packs. An electronic-based cold source is also contemplated.

While the invention has been illustrated and described as an arrangement for providing cold therapy relief, e.g., by treating menopause-associated vasomotor symptoms in accordance with a method of performing such treatment, it is not intended to be limited to the details shown, since various modifications and structural changes may be made without departing in any way from the spirit of the present invention. For example, as noted above, the arrangement can be used for treating any person with cold therapy at any human body site requiring to be cooled. The body site can be, for example, an injured or swollen area, or an area made hot after exposure to radiation or chemotherapy, etc. The body site need not be on the user's own body; it is also contemplated that the body site could be on another person, e.g., a child, requiring cold therapy relief, e.g., as a result of an injury, or even on a non-human, e.g., an animal or pet.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention and, therefore, such adaptations should and are intended to be comprehended within the meaning and range of equivalence of the following claims.

What is claimed as new and desired to be protected by Letters Patent is set forth in the appended claims.

I claim:

1. An arrangement for cooling a body site, comprising:
    a thermally insulated housing;
    a cold source mounted in the thermally insulated housing and formulated to be cooled to a first cooled state when cooled to a cold temperature, the cold source being removable from the thermally insulated housing;
    a cold pack mounted in the thermally insulated housing and formulated to be cooled to a second cooled state different in malleability than the first cooled state when cooled to the cold temperature, the cold pack being in cooling communication with the cold source in the thermally insulated housing, the cold pack being separate from the cold source and being separately removable from the thermally insulated housing for external application to the body site; and
    an additional cold pack mounted in the thermally insulated housing, each cold pack being re-usable and re-coolable and comprises a bag containing an aqueous gel having water-swellable polymeric components.

2. The arrangement of claim 1, and a disposable cover for containing each cold pack during the external application of each cold pack.

3. The arrangement of claim 2, wherein the disposable cover is mounted in the thermally insulated housing prior to the external application of each cold pack.

4. The arrangement of claim 1, wherein the cold source is in direct surface area contact with the each cold pack in a closed condition of the thermally insulated housing.

5. The arrangement of claim 1, and a disposable cover for covering each cold pack, and wherein the cold source is in direct surface area contact with the cover in a closed condition of the thermally insulated housing.

6. The arrangement of claim 1, wherein the thermally insulated housing has housing parts, and thermal insulation for insulating at least one of the housing parts.

7. The arrangement of claim 1, wherein the thermally insulated housing is covered by a fabric.

8. The arrangement of claim 1, and a fastener for opening and closing the thermally insulated housing.

9. The arrangement of claim 1, wherein the thermally insulated housing has housing parts, and wherein at least one of the housing parts has an outwardly bulging shape.

10. A method of cooling a body site, comprising the steps of:
    mounting cold packs and a separate cold source in a thermally insulated housing;
    formulating the cold source to be cooled to a first cooled state when cooled to a cold temperature;
    formulating each cold pack to be cooled to a second cooled state different in malleability than the first cooled state when cooled to the cold temperature, each cold pack comprising a bag containing an aqueous gel having water-swellable polymeric components;
    simultaneously cooling the thermally insulated housing, together with each cold pack and the cold source, to the cold temperature;
    removing the cold source from the thermally insulated housing;
    removing each cold pack from the thermally insulated housing; and
    externally applying each removed cold pack to the body site, each cold pack being re-usable and re-coolable.

11. The method of claim 10, wherein the cooling step is performed by placing the thermally insulated housing, together with each cold pack and the cold source, in a freezer.

12. An arrangement for cooling a human body site for cold therapy relief of menopausal symptoms, comprising:
    a thermally insulated housing;
    a cold source mounted in the thermally insulated housing and comprising a bag containing an aqueous gel formulated to assume a rigid state when cooled to a cold temperature, the cold source being removable from the thermally insulated housing;
    re-usable, re-coolable, cold packs mounted in the thermally insulated housing, each cold pack comprising a bag containing an aqueous gel having water-swellable polymeric components formulated to retain a malleable state when cooled to the cold temperature, each cold pack being in cooling communication with the cold source in the thermally insulated housing, each cold pack being separate from the cold source and being separately removable from the thermally insulated housing for external application to the human body site; and a disposable cover for containing each cold pack during the external application of each cold pack.

13. An arrangement for cooling a body site, comprising:

a thermally insulated housing;

a cold source mounted in the thermally insulated housing and formulated to be cooled to a first cooled state when cooled to a cold temperature;

a cold pack mounted in the thermally insulated housing and formulated to be cooled to a second cooled state different in malleability than the first cooled state when cooled to the cold temperature, the cold pack being in cooling communication with the cold source in the thermally insulated housing, the cold pack being removable from the thermally insulated housing for external application to the body site; and an additional cold pack mounted in the thermally insulated housing, each cold pack being re-usable and re-coolable and comprises a bag containing an aqueous gel having water-swellable polymeric components.

14. The arrangement of claim 13, wherein the cold source is in cooling communication with each cold pack in the thermally insulated housing.

15. An arrangement for cooling a body site, comprising:

a thermally insulated housing having compartments;

a cold source mounted in the thermally insulated housing in one of the compartments and formulated to be cooled to a first cooled state when cooled to a cold temperature;

a cold pack mounted in the thermally insulated housing in another of the compartments and formulated to be cooled to a second cooled state different in malleability than the first cooled state when cooled to the cold temperature, the cold pack being in cooling communication with the cold source in the thermally insulated housing, the cold pack being removable from the thermally insulated housing for external application to the body site; and an additional cold pack mounted in the thermally insulated housing, each cold pack being re-usable and re-coolable and comprises a bag containing an aqueous gel having water-swellable polymeric components.

16. An arrangement for cooling a body site, comprising:

a thermally insulated housing having housing parts that are pivotably interconnected;

a cold source mounted in the thermally insulated housing and formulated to be cooled to a first cooled state when cooled to a cold temperature;

a cold pack mounted in the thermally insulated housing and formulated to be cooled to a second cooled state different in malleability than the first cooled state when cooled to the cold temperature, the cold pack being in cooling communication with the cold source in the thermally insulated housing, the cold pack being removable from the thermally insulated housing for external application to the body site; and an additional cold pack mounted in the thermally insulated housing, each cold pack being re-usable and re-coolable and comprises a bag containing an aqueous gel having water-swellable polymeric components.

17. An arrangement for cooling a body site, comprising:

a thermally insulated housing having an internal compartment, and a mesh at least partly overlying the internal compartment;

a cold source mounted in the thermally insulated housing and formulated to be cooled to a first cooled state when cooled to a cold temperature;

a cold pack mounted in the thermally insulated housing and formulated to be cooled to a second cooled state different in malleability than the first cooled state when cooled to the cold temperature, the cold pack being in cooling communication with the cold source in the thermally insulated housing, the cold pack being removable from the thermally insulated housing for external application to the body site; and an additional cold pack mounted in the thermally insulated housing, each cold pack being re-usable and re-coolable and comprises a bag containing an aqueous gel having water-swellable polymeric components.

18. A method of cooling a body site, comprising the steps of:

mounting cold packs and a cold source in a thermally insulated housing;

simultaneously cooling the thermally insulated housing, together with each cold pack and the cold source, to a cold temperature;

formulating the cold source to be cooled to a first cooled state when cooled to the cold temperature;

formulating each cold pack to be cooled to a second cooled state different in malleability than the first cooled state when cooled to the cold temperature, each cold pack comprising a bag containing an aqueous gel having water-swellable polymeric components;

removing each cold pack from the thermally insulated housing; and externally applying each removed cold pack to the body site, each cold pack being re-usable and re-coolable.

19. A method of cooling a body site, comprising the steps of:

mounting cold packs and a cold source in a thermally insulated housing;

simultaneously cooling the thermally insulated housing, together with each cold pack and the cold source, to a cold temperature;

formulating the cold source to be cooled to a first cooled state when cooled to the cold temperature;

formulating each cold pack to be cooled to a second cooled state different in malleability than the first cooled state when cooled to the cold temperature, each cold pack comprising a bag containing an aqueous gel having water-swellable polymeric components;

removing each cold pack from the thermally insulated housing;

externally applying each removed cold pack to the body site, each cold pack being re-usable and re-coolable; and covering each cold pack with a disposable cover during the externally applying step.

20. A method of cooling a body site, comprising the steps of:

mounting cold packs and a cold source in a thermally insulated housing;

simultaneously cooling the thermally insulated housing, together with each cold pack and the cold source, to a cold temperature, the cooling step being performed in an opened condition of the thermally insulated housing;

formulating the cold source to be cooled to a first cooled state when cooled to the cold temperature;

formulating each cold pack to be cooled to a second cooled state different in malleability than the first cooled state when cooled to the cold temperature, each cold pack comprising a bag containing an aqueous gel having water-swellable polymeric components;

removing each cold pack from the thermally insulated housing; and externally applying each removed cold pack to the body site, each cold pack being re-usable and re-coolable.

21. A method of cooling a body site, comprising the steps of:

mounting cold packs and a cold source in a thermally insulated housing;

simultaneously cooling the thermally insulated housing, together with each cold pack and the cold source, to a cold temperature, the cooling step being performed in a closed condition of the thermally insulated housing;

formulating the cold source to be cooled to a first cooled state when cooled to the cold temperature;

formulating each cold pack to be cooled to a second cooled state different in malleability than the first cooled state when cooled to the cold temperature, each cold pack comprising a bag containing an aqueous gel having water-swellable polymeric components;

removing each cold pack from the thermally insulated housing; and externally applying each removed cold pack to the body site, each cold pack being re-usable and re-coolable.

* * * * *